United States Patent
Dovichi et al.

(10) Patent No.: US 10,578,580 B2
(45) Date of Patent: Mar. 3, 2020

(54) ONE-STEP CAPILLARY ISOELECTRIC FOCUSING AND MOBILIZATION OF ANALYTES

(71) Applicant: UNIVERSITY OF NOTRE DAME DU LAC, South Bend, IN (US)

(72) Inventors: Norman Dovichi, South Bend, IN (US); Guijie Zhu, South Bend, IN (US); Liangliang Sun, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 15/741,883

(22) PCT Filed: Sep. 22, 2017

(86) PCT No.: PCT/US2017/052952
§ 371 (c)(1),
(2) Date: Jan. 4, 2018

(87) PCT Pub. No.: WO2018/057885
PCT Pub. Date: Mar. 29, 2018

(65) Prior Publication Data
US 2019/0004010 A1     Jan. 3, 2019

Related U.S. Application Data
(60) Provisional application No. 62/399,267, filed on Sep. 23, 2016.

(51) Int. Cl.
*G01N 27/447*     (2006.01)
*G01N 30/72*     (2006.01)
(Continued)

(52) U.S. Cl.
CPC ......... *G01N 27/44795* (2013.01); *C07K 1/28* (2013.01); *G01N 27/447* (2013.01);
(Continued)

(58) Field of Classification Search
CPC . G01N 27/447; G01N 27/44795; G01N 30/72
See application file for complete search history.

(56) References Cited

U.S. PATENT DOCUMENTS
8,097,472 B2    1/2012    Schneider et al.
9,927,399 B2    3/2018    Shimura et al.
(Continued)

FOREIGN PATENT DOCUMENTS
WO     2008006201 A1     1/2008
WO     WO-2015031820 A1 *     3/2015  ......... G01N 27/4473

OTHER PUBLICATIONS
G. Zhu, L. Sun, and N. Dovichi, Simplified capillary isoelectric focusing with chemical mobilization for intact protein analysis, 40, Journal of Separation Science, 2017, p. 948-53. (Year: 2017).*
(Continued)

*Primary Examiner* — Luan V Van
*Assistant Examiner* — Caitlyn Mingyun Sun
(74) *Attorney, Agent, or Firm* — Haukaas Fortius PLLC; Michael H. Haukaas (57) ABSTRACT

The invention provides a capillary isoelectric focusing (cIEF) system based on a sandwich injection method for automated chemical mobilization. This system was coupled with an electrokinetically pumped nanoelectrospray interface to a mass spectrometer. The nanoelectrospray emitter employed an acidic sheath electrolyte. To realize automated focusing and mobilization, a plug of ammonium hydroxide was first injected into the capillary, followed by a section of mixed sample and ampholyte. As focusing progressed, the $NH_3H_2O$ section was titrated to lower pH buffer by the
(Continued)

acidic sheath buffer. Chemical mobilization started automatically once the ammonium hydroxide was consumed by the acidic sheath flow electrolyte.

20 Claims, 4 Drawing Sheets

(51) Int. Cl.
*G01N 30/00* (2006.01)
*C07K 1/28* (2006.01)
(52) U.S. Cl.
CPC ....... *G01N 27/44743* (2013.01); *G01N 30/72* (2013.01); *G01N 27/44717* (2013.01); *G01N 2030/009* (2013.01)

(56) References Cited

U.S. PATENT DOCUMENTS

| | | | |
|---|---|---|---|
| 2005/0161332 | A1 | 7/2005 | Vigh |
| 2013/0140180 | A1 | 6/2013 | Dovichi et al. |
| 2015/0162177 | A1* | 6/2015 | McGivney ........... G01N 27/447 250/282 |
| 2015/0311056 | A1 | 10/2015 | Dovichi et al. |

OTHER PUBLICATIONS

Dada et al., "Capillary Array Isoelectric Focusing with Laser-induced Fluorescence Detection: Milli-pH unit Resolution and Yoctomole Mass Detection Limits in a 32-channel System," Anal Bioanal Chem. 397:3305-3310, Mar. 2010.
International Search Report and Written Opinion of the ISA/US dated Dec. 5, 2017 in International Application No. PCT/US2017/052952; 8 pgs.
Ramsay et al., "Capillary Isoelectric Focusing with ph 9.7 Cathode for the Analysis of Gastric Biopsies," Anal Bioanal Chem., 400(7):2025-2030, Jun. 2011.
Righetti et al., "Capillary Electrophoresis and Isoelectric Focusing in Peptide and Protein Analysis," Proteomics, 13(2):325-340, Jan. 2013.
Sun et al., "Third-Generation Electrokinetically Pumped Sheath—Flow Nanospray Interface with Improved Stability and Sensitivity for Automated Capillary Zone Electrophoresis-Mass Spectrometry Analysis of Complex Proteome Digests," J Proteome Res., 14(5):2312-2321, May 2015.
Sun et al., "Ultrasensitive and Fast Bottom-up Analysis of Femtogram Amounts of Complex Proteome Digests," Angew Chem Int Ed Engl., 52(51):13661-13664, Dec. 2013.
Zhu et al., "A Rapid cIEF-ESI-MS/MS Method for Host Cell Protein Analysis of a Recombinant Human Monoclonal Antibody," Talanta., 98:253-256, Aug. 2012.
Zhu et al., "Bottom-Up Proteomics of *Escherichia coli* Using Dynamic pH Junction Preconcentration and Capillary Zone Electrophoresis—Electrospray Ionization—Tandem Mass Spectrometry," Anal. Chem., 86(13):6331-6336, May 2014.
Zhu et al., "Capillary Isoelectric Focusing—Tandem Mass Spectrometry and Reversed-Phase Liquid Chromatography—Tandem Mass Spectrometry for Quantitative Proteomic Analysis of Differentiating PC12 Cells by Eight-Plex Isobaric Tags for Relative and Absolute Quantification," Anal Chem., 85(15):7221-7229, Aug. 2013.
Zhu et al., "Simplified Capillary Isoelectric Focusing with Chemical Mobilization for Intact Protein Analysis," J Sep Sci., 40(4):948-953, Feb. 2017.
Zhu et al., "Thermally-Initiated Free Radical Polymerization for Reproducible Production of Stable Linear Polyacrylamide Coated Capillaries, and their Application to Proteomic Analysis Using Capillary Zone Electrophoresis—Mass Spectrometry," Talanta, 146:839-843, Jan. 2016.
Zhu wt al., "On-line Amino Acid-based Capillary Isoelectric Focusing-ESI-MS/MS for Protein Digests Analysis," Anal Chim. Acta., 750:207-211, Oct. 2012.
Extended Search Report and Written Opinion of the European Patent Office dated Aug. 16, 2018 in EP Application No. 17828636.5; 9pgs.
Hühner et al., "Capillary Isoelectric Focusing—Mass Spectrometry: Coupling Strategies and Applications," Electrophoresis, 36(21-22):2670-2686, Nov. 2015.
Zhong et al., "Flow-Through Microvial Facilitating Interface of Capillary Isoelectric Focusing and Electrospray Ionization Mass Spectrometry," Anal. Chem., 83(22):8748-8755, Oct. 2011.

* cited by examiner

ONE-STEP CAPILLARY ISOELECTRIC FOCUSING AND MOBILIZATION OF ANALYTES

RELATED APPLICATIONS

This application claims priority under 35 U.S.C. § 119(e) to U.S. Provisional Patent Application No. 62/399,267, filed Sep. 23, 2016, which is incorporated herein by reference.

GOVERNMENT SUPPORT

This invention was made with government support under Grant No. R01 GM096767 awarded by the National Institutes of Health. The government has certain rights in the invention.

BACKGROUND OF THE INVENTION

Capillary isoelectric focusing (cIEF), which was first demonstrated by Hjertén and Zhu (*J. Chomatogr.* 1985, 346, 265), has proven to be a powerful method for protein and peptide analysis. cIEF is typically performed as a two-step process, with a focusing (separation) step followed by a mobilization step. During focusing, proteins or peptides are separated based on their isoelectric point (pI). Optical detection can be used to image the focused bands within the separation capillary.

Alternatively, the focused sample is mobilized to a detector placed at the capillary's distal end. Two kinds of mobilization approaches are typically employed. Hydraulic mobilization is produced using pressure, vacuum, or syphon. Alternatively, chemical mobilization, as first proposed by Hjertén (*J. Chromatogr.* 1987, 387, 127-138), is performed by changing the catholyte to lower pH buffer. Chemical mobilization avoids Taylor dispersion due to laminar flow during pressure mobilization.

cIEF has been coupled to a range of detectors, including UV absorbance, laser-induced fluorescence, and mass spectrometry. Mass spectrometry provides information-rich identification such as accurate molecular weight and fragmentation information. Although there are some challenges for on-line coupling cIEF to mass spectrometry, several reports have analyzed complex mixtures of proteins or peptides.

However, earlier cIEF-MS experimental methods employed chemical mobilization that required significant manual manipulation of the capillary. Focusing was performed off-line using appropriate buffers in dedicated reservoirs. After focusing, the capillary was manually inserted into the emitter, where the acidic sheath electrolyte served as mobilization buffer and generated chemical mobilization to drive the samples to the mass spectrometer. This manual operation is time-consuming, tedious, frustrates automation, and limits the practical application of this technique.

Accordingly, there is a need to perform cIEF-MS experiments that do not require cumbersome and significant manual manipulation of the capillary for off-line focusing and chemical mobilization.

SUMMARY

A capillary isoelectric focusing (cIEF) system based on a sandwich injection method for automated chemical mobilization is described herein. This system was coupled with an electrokinetically pumped nanoelectrospray interface to a mass spectrometer (such as an ion trap or time of flight mass spectrometer). The nanoelectrospray emitter employed an acidic sheath electrolyte. To realize automated focusing and mobilization, a plug of ammonium hydroxide was first injected into the capillary, followed by a section of mixed sample and ampholyte. During focusing, the $NH_3H_2O$ section worked as catholyte. As focusing progressed, the $NH_3H_2O$ section was titrated to lower pH buffer by the acidic sheath buffer. Chemical mobilization started automatically once the ammonium hydroxide was consumed by the acidic sheath flow electrolyte, which then acted as the mobilization solution. In this disclosure, the lengths of the $NH_3H_2O$ section and sample were optimized. With a 1-meter long capillary, a relative short plug of the $NH_3H_2O$ section (3 cm) produced both fast migration and reasonable separation resolution. The automated CIEF-MS system produced base peak intensity relative standard deviation of 8.5% and migration time relative standard deviation ≤0.6% for myoglobin and cytochrome C in triplicate runs.

Accordingly, this disclosure provides a method for one-step capillary isoelectric focusing (cIEF) and chemical mobilization, the method comprising:

(a) performing a separation on a separation capillary having an anode end and a cathode end, wherein the cathode end of the separation capillary is interfaced to an electrokinetically pumped nanoelectrospray emitter on a mass spectrometer;

(b) partially filling the anode end of the separation capillary, first, with a length of a catholyte solution, then second, with a mixture comprising an ampholyte and analytes;

(c) feeding the nanoelectrospray emitter with an acidic sheath electrolyte solution and an anolyte solution, wherein the anolyte solution feeds into the nanoelectrospray emitter by flowing out from the cathode end of the separation capillary;

(d) applying a voltage to the anode and cathode ends of the separation capillary;

(e) inducing isoelectric focusing of the analytes and concomitant chemical mobilization of the analytes toward the cathode end of the separation capillary; and (f) forming a nanoelectrospray, wherein the acidic sheath electrolyte solution ensheaths the mixture flowing out the cathode end of the separation capillary;

wherein a pH gradient is established by the catholyte solution and the anolyte solution to induce isoelectric focusing of the analytes, and as the catholyte solution is titrated to lower pH by the acidic sheath electrolyte solution the analytes are chemically mobilized, then electrokinetically pumped toward the mass spectrometer by the acidic sheath electrolyte solution, thereby forming the nanoelectrospray when the voltage is applied.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3A-3C. Base peak electropherograms of mixture of cytochrome C (1), myoglobin (2), beta-lactoglublin (3), and carbonic anhydrase (4) using the automated cIEF-MS/MS system with a 3-cm long 0.3% $NH_3H_2O$ plug length and 50-cm (A), 60-cm (B) and 80-cm (C) sample plug length.

DETAILED DESCRIPTION

In capillary isoelectric focusing methods, the analytes are separated during a focusing step. To be detected and isolated, the analytes must be moved past the point of detection. This separate process follows the focusing step. The point of detection in a capillary electrophoresis instrument is placed towards the outlet end of the separation capillary. Once the protein or peptide mixture has been sorted according to their pI in the cIEF process, the individual analyte zones are distributed along the capillary from lowest to highest pI before the point of detection. Thus, the analyte zones must be moved toward the capillary outlet to pass the point of detection (See Agilent Technologies primer, 5991-1660EN, by T. Kristl et al., *Principles and Application of Capillary Isoelectric Focusing* 2014). An approach that has become established for this purpose is chemical mobilization. In practical terms, this has been a manual two-step process that is cumbersome.

In chemical mobilization, the anolyte or catholyte is replaced by another electrolyte solution with high ionic strength or different pH. The sample analytes and carrier ampholytes acquire a net charge and start to move towards the outlet thereby passing the point of detection. For example, a solution of weak acid can be used to replace the catholyte. The negative ions from the chemical mobilizer (the weak acid) enter the capillary from the cathodic side, whereas the hydronium ions from the anolyte enter the capillary from the anodic side. The pH gradient is disrupted by the weak acid and carrier ampholytes, and analytes are provided with a net positive charge which leads to their mobilization towards the cathode, the capillary side where the point of detection is situated. Thus, the manual two-step process described above has been reduced to one-step by the disclosed sandwich injection method.

Additionally, our group has previously developed an electrokinetically driven sheath-flow nanospray interface for capillary electrophoresis-MS that provides extremely stable and low sheath flow rates. We coupled cIEF to ESI-MS for analysis of a product-depleted, recombinant therapeutic sample and identified 53 peptides corresponding to 37 host cell proteins in a rapid analysis. We also developed the use of amino acids to generate the pH gradient in isoelectric focusing and identified over 100 proteins and 300 peptides from a RAW 264.7 tryptic digest. We have also used cIEF with amino-acid ampholytes for the quantitative proteomic analysis of iTRAQ labeled PC12 cells differentiation after treatment with nerve growth factor. And a total of 2,329 peptides and 835 protein groups were quantitated. Ninety-six differentially expressed proteins were identified.

In this disclosure, a sandwich injection method to automate cIEF-MS based on a electrokinetically driven sheath-flow CE-MS nanospray interface is described.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "separation capillary" generally refers to a tubular device with a narrow bore that is capable of separating analytes into purified substances within its inner surface and over its length. The separation capillary can be made or a variety of substances. It may comprise a coating, a stationary phase, a mobile phase, or a combination thereof.

The term "electrophoresis" refers to separation of analytes bases on the differential speed of movement of charged species in an electric field.

The term "electroosmotic flow" refers to a characteristic of electrophoresis. When an electric field is applied to an electrolyte solution, for example, along the axis of a separation capillary, the excess of cations close to the wall of the capillary, which are mobile, are drawn to the electrode of the opposite charge dragging along their solvation shell. The electroosmotic flow phenomenon also occurs in the glass emitter of an electrospray interface when a potential applied to a reservoir of sheath electrolyte electrokinetically drives (or pumps) the sheath fluid through the interface to generate an electrospray.

The term "ampholyte" refers to amphoteric molecules that contain both acidic and basic groups and will exist mostly as zwitterions in a certain range of pH (for example, proteins and polypeptides). The pH at which the average charge is zero is known as the molecule's isoelectric point (pI). Ampholytes are used to establish a stable pH gradient for use in isoelectric focusing.

The terms "anolyte" and "catholyte" refer to different electrolyte species in solution, wherein anolyte is localized near the anode and the catholyte is localized near the cathode.

The term "length", as used herein, refers to a volume of solution, for example, a sample comprising a mixture of ampholytes and analytes, that has a length in a separation capillary having a certain inner diameter. The term "length" as used herein, is also synonymous with the term "plug". For example, a plug of a sample, or a plug of a catholyte, refers to a solution of a sample, or a solution of a catholyte, that has been, for instance, injected or somehow introduced into a capillary, wherein the volume of the solution of the sample or the catholyte that was introduced has a length inside the capillary that is a fraction (or percentage) of the total length of the capillary.

Embodiments of the Invention

In various embodiments, a method for one-step capillary isoelectric focusing (cIEF) and chemical mobilization is disclosed, the method comprising:
(a) performing a separation on a separation capillary having an anode end and a cathode end, wherein the cathode end of the separation capillary is interfaced to an electrokinetically pumped nanoelectrospray emitter on a mass spectrometer;
(b) partially filling the anode end of the separation capillary, first, with a length of a catholyte solution, then second, with a mixture comprising an ampholyte and analytes;
(c) feeding the nanoelectrospray emitter with an acidic sheath electrolyte solution and an anolyte solution, wherein the anolyte solution feeds into the nanoelectrospray emitter by flowing out from the cathode end of the separation capillary;
(d) applying a voltage to the anode and cathode ends of the separation capillary;
(e) inducing isoelectric focusing of the analytes and concomitant chemical mobilization of the analytes toward the cathode end of the separation capillary; and (f) forming a nanoelectrospray, wherein the acidic sheath electrolyte solution ensheaths the mixture flowing out the cathode end of the separation capillary;

wherein a pH gradient is established by the catholyte solution and the anolyte solution to induce isoelectric focusing of the analytes, and as the catholyte solution is titrated to lower pH by the acidic sheath electrolyte solution the analytes are chemically mobilized, then electrokinetically pumped toward the mass spectrometer by the acidic sheath electrolyte solution, thereby forming the nanoelectrospray when the voltage is applied. One or more of elements (a)-(f) above may be optionally omitted from the method in various embodiments.

In additional embodiments the separation capillary is a silica capillary, a fused silica capillary, or a capillary used for separating analytes. In other embodiments, the separation capillary is a glass or a polymer. In yet other embodiments, the separation capillary is coated or uncoated.

In additional embodiments, the catholyte solution has a length in the separation capillary of about or at least 1 cm, 2 cm, 3 cm, 4 cm. 5 cm, 6 cm, 7 cm, 8 cm, 9 cm, 10 cm, 15 cm, 20 cm, 30 cm, 40 cm, 50 cm, 75 cm, or 100 cm upon initial filling. In yet other embodiments, the catholyte solution has a length in the separation capillary, wherein the length of the capillary is expressed as a fraction or percentage (%) of the length of the separation capillary. For example, in various embodiments, the length of the capillary solution as a percent of the length of the silica capillary is about 1% to about 99%, about 2% to about 80%, about 4% to about 60%, about 5% to about 50%, about 5% to about 40%, about 5% to about 30%, about 5% to about 20%, about 5% to about 10%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%.

In various embodiments, the inner diameter of the separation capillary is about or less than 1 mm, 0.5 mm, 0.4 mm, 0.3 mm, 0.25 mm, 0.2 mm, 0.1 mm, 0.05 mm, 0.025 mm, 0.01 mm, or 0.005 mm.

This disclosure includes various embodiments of mass spectrometers (MS) that can be adapted to the methods described herein. For example, the type of mass spectrometer can be, but is not limited to, an ion trap mass spectrometer, a time of flight mass spectrometer, an inductively coupled plasma-MS, a matrix assisted laser desorption ionization MS, a surface enhanced laser desorption ionization MS, a tandem MS, or a combination of the aforementioned mass spectrometer types thereof.

In other embodiments, the catholyte solution comprises ammonium hydroxide, sodium hydroxide, or any alkaline solution. The alkaline catholyte solution can be 0.01M to 15M, or 0.1% v/v to 99% v/v base. In various other embodiments, the mixture comprising an ampholyte and analytes has a length in the separation capillary of at least 1 cm, 2 cm, 3 cm, 4 cm. 5 cm, 6 cm, 7 cm, 8 cm, 9 cm, 10 cm, 15 cm, 20 cm, 30 cm, 40 cm, 50 cm, 75 cm, or 100 cm upon initial filling. In various additional embodiments, the length of the mixture as a percent of the length of the silica capillary is about 1% to about 99%, about 2% to about 80%, about 4% to about 60%, about 5% to about 50%, about 5% to about 40%, about 5% to about 30%, about 5% to about 20%, about 5% to about 10%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%.

In additional embodiments, the mixture comprises one or more ampholytes and one or more analytes.

In yet other embodiments, the anolyte solution comprises a $(C_1-C_8)$carboxylic acid such as formic acid, acetic acid, propionic acid, or butyric acid, and/or a mineral acid such as sulfuric acid, phosphoric acid, or hydrochloric acid. The anolyte solution can be 0.01M to 15M, or 0.1% v/v to 99% v/v acid.

In various other embodiments, the ampholyte comprises has a high buffering capacity per pH unit, a linear pH gradient, and even conductivity across the ampholyte. In some preferred embodiments, the ampholyte comprises Pharmalyte® 3-10. In other embodiments, the high buffering capacity per pH unit of the ampholyte ranges from pH 3-10, pH 3-4, pH 3-5, pH 3-6, pH 3-7, pH 3-8, pH 4-7, pH 4-8, pH 5-8, pH 5-9, pH 5-10, pH 6-8, pH 6-9, pH 6-10, pH 7-9, pH 7-10, or pH 8-10.

In additional embodiments, the acidic sheath electrolyte solution is a chemical mobilizer. In other embodiments, the acidic sheath electrolyte solution comprises formic acid, acetic acid, a $(C_3-C_8)$carboxylic acid, sulfuric acid, phosphoric acid, hydrochloric acid, or another mineral acid. In some embodiments, the acidic sheath electrolyte solution can be 0.01M to 15M, or 0.1% v/v to 99% v/v acid.

In various embodiments, the acidic sheath electrolyte solution further comprises an organic solvent, an alcohol, or acetonitrile. In some embodiments, the alcohol can be methanol, ethanol, propanol, isopropanol, butanol, or any $(C_1-C_8)$ alcohol. In yet other various embodiments, the acidic sheath electrolyte solution can comprise about 0.1% to about 50% alcohol, or about 1% to about 20% alcohol. In some additional embodiments, the acidic sheath electrolyte solution can comprise about 0.1% to about 50% acetonitrile, or about 1% to about 20% acetonitrile.

In additional embodiments, the voltage applied for isoelectric focusing and chemical mobilization ranges from about 50 V/cm to about 500 V/cm, about 100 V/cm to about 400 V/cm, or about 150 V/cm to about 350 V/cm. In other embodiments, chemical mobilization automatically follows isoelectric focusing without manual physical manipulation of the separation capillary.

In yet other embodiments, the separation capillary has an inner surface coated with a polymer. In various other embodiments, the polymer comprises a linear polyacrylamide, linear polyacrylamide (LPA), or any polymer suitable for cIEF. In additional embodiments, the separation capillary has a length of at least 10 cm, 20 cm, 50 cm, 100 cm, 500 cm, 1 m, 2 m, 5 m, 10 m, or 100 m.

In other embodiments, the outer diameter of the tip of the cathode end of the separation capillary is reduced relative to the outer diameter of the remainder of the separation capillary. In additional embodiments, the tip having a reduced outer diameter of a distal end of the capillary has a length of less than 5 mm, 3 mm, 2 mm, 1 mm, 0.5 mm, 0.25 mm, 0.1 mm, 0.05 mm, or 0.02 mm. In various embodiments, the outer diameter of the tip can be reduced by about 1% to about 80%, about 5% to about 50%, or about 10% to about 30%.

In various other embodiments, the outer diameter of the tip of the cathode end of the separation capillary is 20%-50% larger than the inner diameter of the separation capillary. In other embodiments, the outer diameter of the tip of the cathode end of the separation capillary is about 10%, 25%, 30%, 35%, 40%, 45%, 50%, 60%, 70%, or 80% larger than the inner diameter of the separation capillary.

In yet additional embodiments, the mixture comprising an ampholyte and analytes comprises more than one different analyte. In other embodiments, the analytes comprise peptides, proteins, or drug-protein conjugates. In various embodiments, the peaks of an electropherogram of proteins, or drug-protein conjugates detected by the mass spectrometer are substantially resolved, partially resolved, or entirely resolved. In other embodiments, the electropherogram is substantially reproducible, or completely reproducible.

Various embodiments of the above disclosure include a kit for one-step capillary isoelectric focusing (cIEF) and chemical mobilization, the kit comprising (a) the catholyte solution, (b) the anolyte solution, (c) the acidic sheath electrolyte solution, (d) the ampholyte, and optionally (e) instructions for use. In other embodiments of the kit, the catholyte solution comprises ammonium hydroxide, the anolyte solution comprises formic acid, the acidic sheath electrolyte solution comprises formic acid and an organic solvent, such as, methanol or acetonitrile, and the ampholyte, for example, Pharmalyte® 3-10. In some embodiments, the instructions are included, and the instructions describe the intended method of use disclosed herein.

Results and Discussion

Experiment Design.

Figure 1:
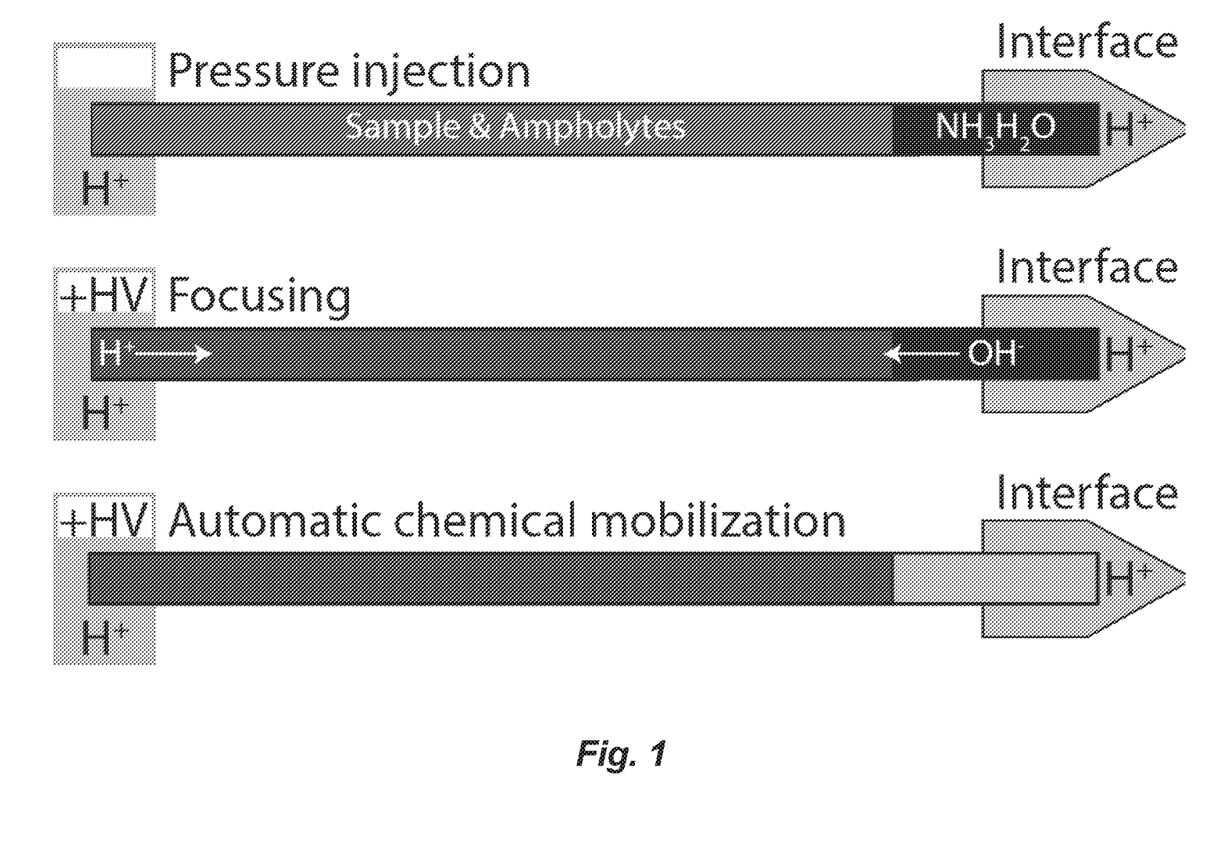
FIG. 1. A diagram of automated CIEF-MS based on electrokinetically pumped electrospray interface FIG. 2A-2D. Base peak electropherograms of a mixture of myoglobin and cytochrome C from automated CIEF-MS/MS with 60 cm sample injection and 1 cm (A), 3 cm (B), 5 cm (C), and 10 cm (D) 0.3% $NH_3H_2O$ plug length.

The electrokinetically driven sheath-flow nanospray based automated cIEF-MS employed a sandwich injection method to automate focusing and mobilization. As shown in FIG. 1, the cathode end of capillary was held in an electrospray emitter throughout the cIEF-MS process and the anode end capillary was fixed in a PrinCE autosampler. In the first step of the procedure, a plug of $NH_3H_2O$ was injected into the capillary followed by a plug of a mixture of sample and ampholytes. The anode end of capillary was then placed into a vial of anolyte for cIEF (0.1% formic acid). Application of high voltage initiated focusing, wherein the $NH_3H_2O$ plug served as catholyte for cIEF. After focusing, a pH gradient was established between anolyte and the $NH_3H_2O$ section. Because the amount of $NH_3H_2O$ is limited, this section would be titrated to lower pH values by the acidic sheath electrolyte. Chemical mobilization started automatically upon consumption of the $NH_3H_2O$ plug.

Length of $NH_3H_2O$ Plug.

Figures 2A, 2D:
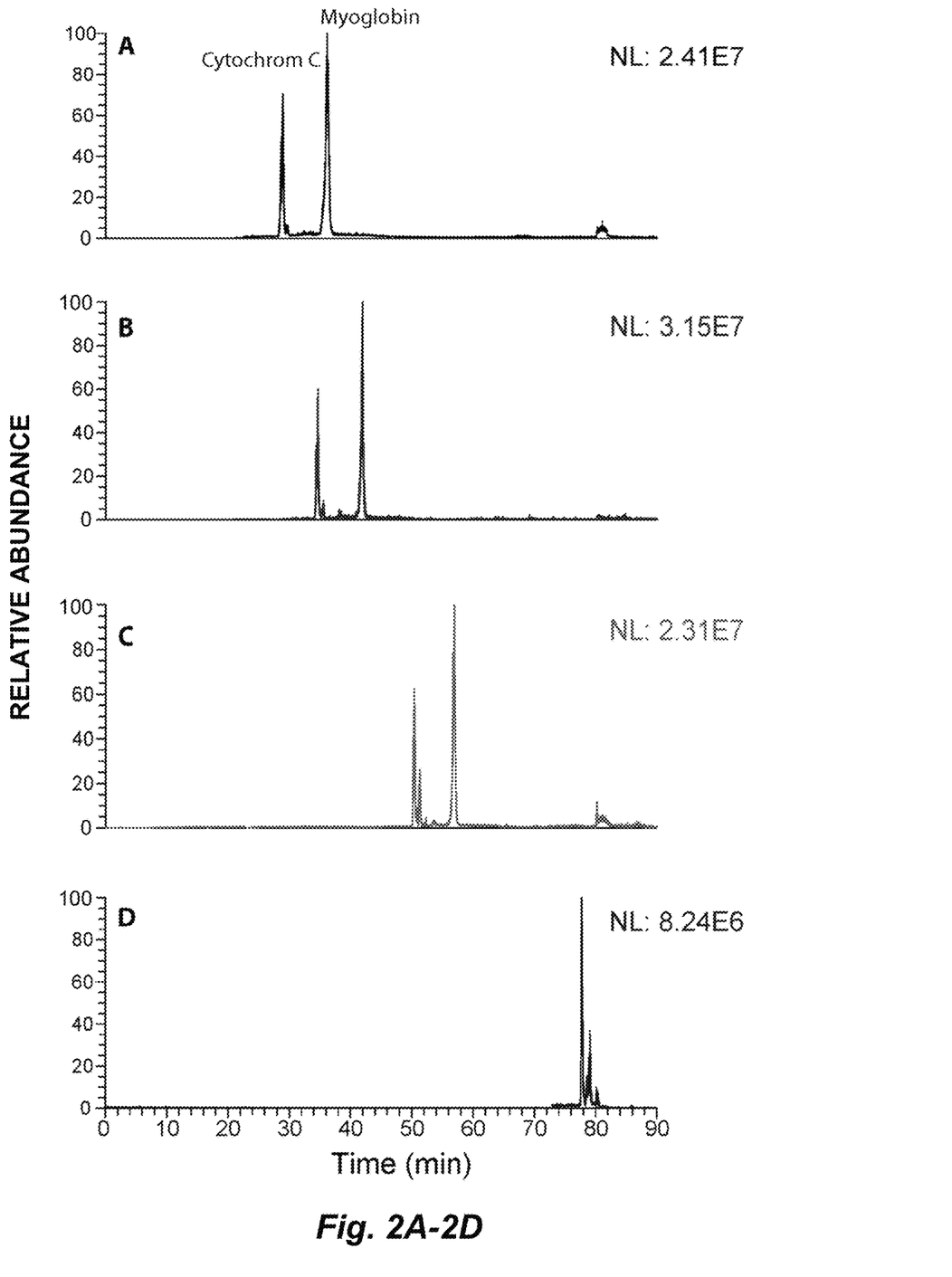

A mixture of cytochrome C and myoglobin was used to investigate the effect of different length of the $NH_3H_2O$ plug on protein separation. FIG. 2 shows the base peak electropherograms of cytochrome C and myoglobin generated by cIEF-MS with the same sample plug length (60 cm) and different $NH_3H_2O$ plug lengths (1 cm, 3 cm, 5 cm, and 10 cm). With a 10 cm long $NH_3H_2O$ plug, components migrated after 80 min, the separation had poor resolution, and the signal intensity was low. In contrast, electropherograms generated with 5 cm, 3 cm, and 1 cm long $NH_3H_2O$ plug lengths produced similar separation resolution, and the migration time decreased in proportion to the $NH_3H_2O$ plug length. The 3 cm long $NH_3H_2O$ plug generated the highest signal intensity. Due to the acceptable migration time, good separation resolution, and high signal intensity, a 3 cm long $NH_3H_2O$ plug length was chosen for subsequent experiments.

Length of Sample Plug.

Figures 3A, 3C:
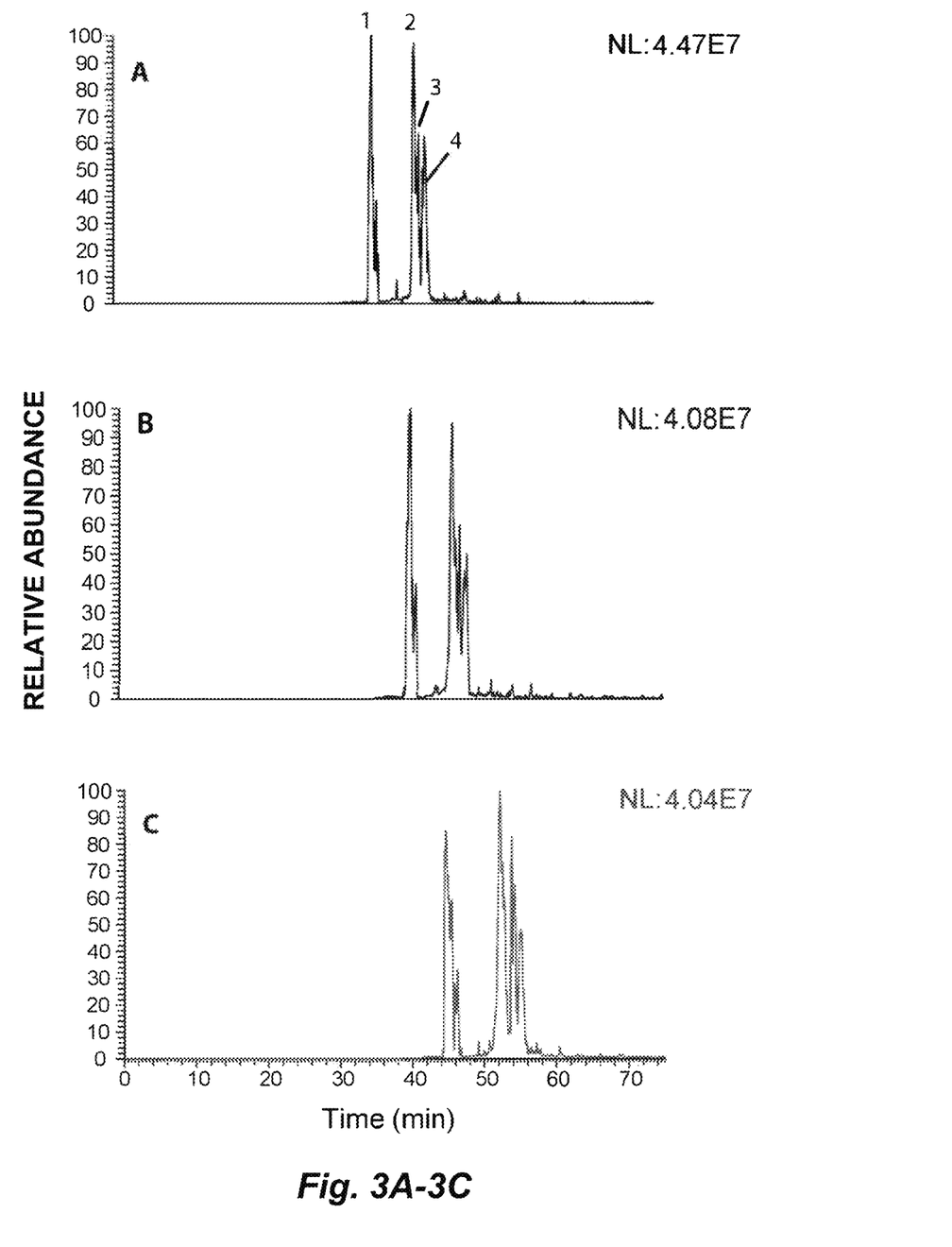

The mixture of cytochrome C (pI 10), myoglobin (pI 7), beta-lactoglobulin (pI 5.1), and carbonic anhydrase (pI 5.4) was used to investigate the effect of sample plug length on the protein separation. FIG. 3 shows the base peak electropherograms of the four proteins by cIEF-MS with a 3-cm $NH_3H_2O$ plug length and different sample plug lengths (50 cm, 60 cm, and 80 cm). Longer sample plugs tend to produce longer migration times and better separation resolution. We also noticed that beta-lactoglobulin with a lower pI (5.1) value migrated faster than carbonic anhydrase with slightly higher pI value (5.4). This shift might be caused by the relatively long chemical mobilization, which adds a component of zone electrophoresis to the separation. The molecular weight of beta-lactoglobulin is 18 kDa, which is much smaller than that of carbonic anhydrase (29 kDa). Due to the smaller molecular weight and similar pI value, beta-lactoglobulin will presumably have a smaller size to charge ratio, and move faster than carbonic anhydrase, which could cause the migration order of these two proteins to switch. This mixed mode separation is a limitation of this form of chemical mobilization in cIEF.

Reproducibility of Automated CIEF-MS.

Figure 4:
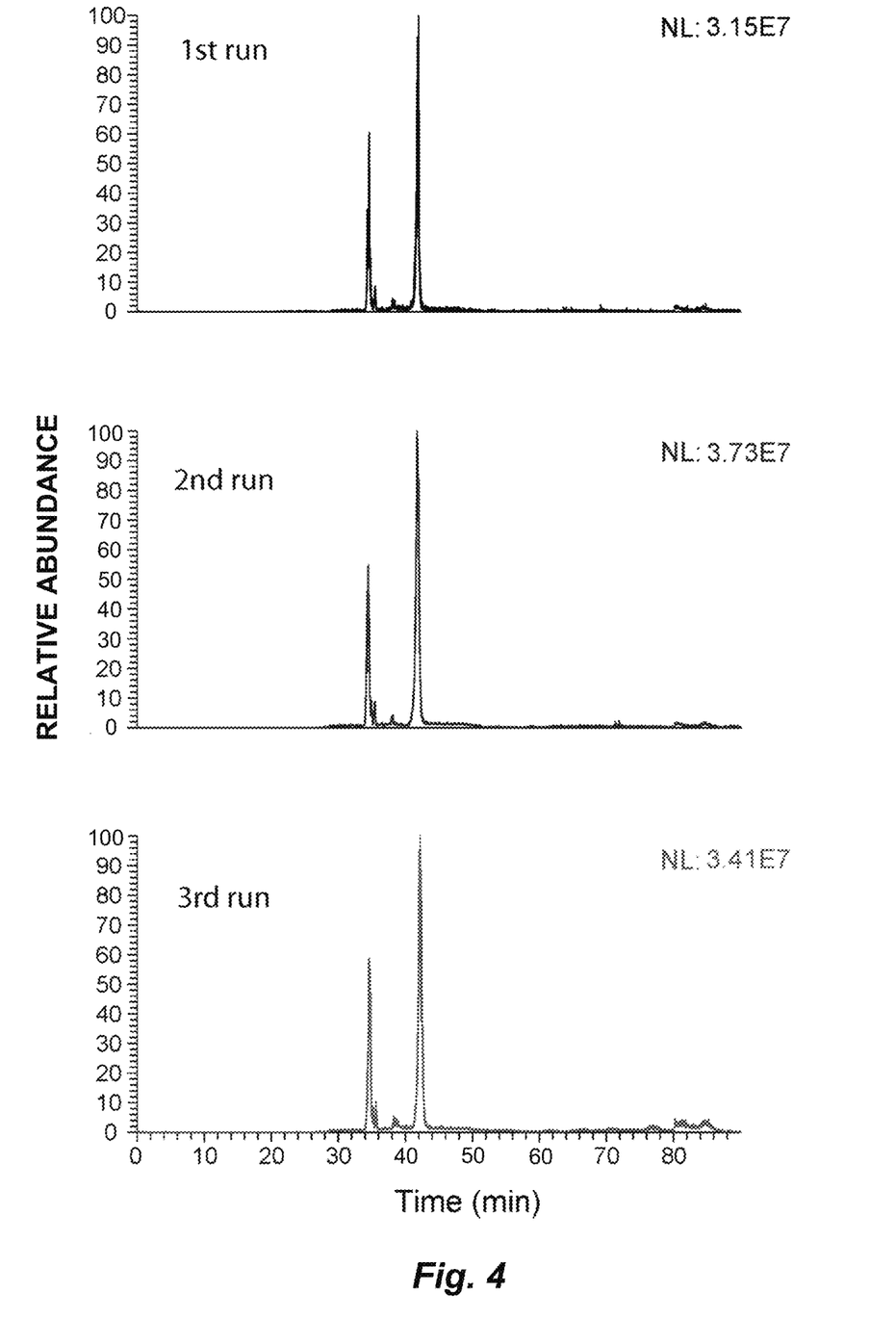
FIG. 4. Base peak electropherograms of triplicate cIEF-MS/MS separation of myoglobin and cytochrome C with 50 cm sample plug length and 3 cm 0.3% $NH_3H_2O$ injection.

The reproducibility of automated cIEF-MS was investigated by separation of cytochrome C and myoglobin. FIG. 4 presents the base peak electropherograms of triplicate runs of cytochrome C and myoglobin by automated CIEF-MS. The RSD of base peak intensity is 8.5%. The RSD of migration time is 0.3% for cytochrome C and 0.6% for myoglobin. These results fully show the outstanding reproducibility of this automated cIEF-MS.

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Experimental Section

Abbreviations.

APS, ammonium persulfate; cIEF, capillary isoelectric focusing; DTT, dithiothreitol; FA, formic acid; IAA, iodoacetamide; LPA, linear polyacrylamide; MS, mass spectrometry.

Reagents.

Acrylamide, ammonium persulfate, cytochrome c from bovine heart, myoglobin from equine skeletal muscle, beta-lactoglobulin from bovine milk, carbonic anhydrase from bovine erythrocyte, urea, ammonium bicarbonate ($NH_4HCO_3$), dithiothreitol (DTT), iodoacetamide (IAA), and 3-(trimethoxysilyl)propyl methacrylate were purchased from Sigma-Aldrich (St. Louis, Mo.). Formic acid (FA) was purchased from Fisher Scientific (Pittsburgh, Pa.). Methanol and water were purchased from Honeywell Burdick & Jackson (Wicklow, Ireland). Ampholytes (Pharmalytes 3-10) were purchased from GE Healthcare (Piscataway, N.J., USA). Uncoated fused silica capillaries (50 µm i.d./365 µm o.d.) were purchased from Polymicro Technologies (Phoenix, Ariz.).

Preparation of Linear Polyacrylamide (LPA) Coated Capillary.

We have reported a simple and reproducible method for preparation of LPA coated capillary (Zhu et al, *Talanta* 2016, 146, 839). The capillary was flushed with 1 M hydrochloric acid for 30 min, water for 10 min, 1 M sodium hydroxide for 30 min, water for 10 min, and finally washed with methanol for 30 min by using a syringe pump at a flow rate of 2 µL/min. The capillary was then dried under a flow of nitrogen at room temperature for 4 hours. Next, 50% (v/v) 3-(trimethoxysilyl) propyl methacrylate in methanol was flushed through the capillary for 10 min. Both ends of the capillary were sealed, and the filled capillary was incubated at room temperature for 24 h. The capillary was then rinsed with methanol for 20 min and dried under nitrogen. 40 mg of acrylamide was dissolved in 1 mL water, and 2 µL of 5%

(w/v) ammonium persulfate (APS) was added to 500 μL of the acrylamide solution. The mixture was vortexed for 30 s and degassed for 5 min using nitrogen. Then the mixture was introduced into a 100 cm length of pretreated capillary by vacuum. With both ends sealed, the capillary was incubated in a 50° C. water bath for 30 min. The capillary then was flushed with water to remove excess reagents, and stored at room temperature before use. A ~1-mm length of the outside of the distal tip of the capillary was etched with HF for 90 min to reduce the outer diameter of the etched part to ~70-μm; the detailed protocol for HF etching is described by Sun et al (*Angew Chem Int Ed Engl.* 2013, 52, 13661).

Preparation of Sample.

A mixture of standard proteins containing cytochrome c (0.05 mg/mL, pI 10), myoglobin (0.15 mg/mL, pI 7), beta-lactoglobulin (0.4 mg/mL, pI 5.1) and carbonic anhydrase (0.15 mg/mL, pI 5.4) dissolved in 2 mM ammonium acetate (pH ~6) buffer was prepared for dynamic pH junction based CZE-MS/MS analysis. The same mixture of proteins was mixed with xx g/mL ampholytes for cIEF analysis.

cIEF-ESI-MS/MS.

A polyacrylamide coated capillary (50 μm i.d., 50 cm long) that was prepared as described above was used for the cIEF separation. A PrinCE autosampler (Prince Technologies B.V., Netherlands) was used for automated injection and separation voltage control. A third-generation electrokinetically driven sheath-flow CE-MS nanospray interface was used to couple the separation with an LTQ-XL (Thermo Fisher Scientific) mass spectrometer. Full MS scans were acquired over the 600-2000 m/z.

Before cIEF-ESI-MS/MS, the capillary was flushed with water at 1,500 mbar pressure for 10 min. During cIEF-MS/MS, the anode end of the capillary was placed in formic acid (0.1%, pH 2.5), and the cathode end was insert into the electrospray emitter (20 μm) that had been filled with the sheath electrolyte (0.1% formic acid with 10% methanol). A plug of 0.3% $NH_3H_2O$ was injected into the capillary using pressure injection at 200 mbar for 0.1 min, 0.3 min, 0.5 min, or 1 min, followed by a plug of sample/ampholytes by using pressure injection at 200 mbar for 5 min, 6 min, or 8 min. The focusing/mobilization voltage was 250 V/cm.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for one-step capillary isoelectric focusing (cIEF) and chemical mobilization, the method comprising:
    (a) performing a separation on a separation capillary having an anode end and a cathode end, wherein the cathode end of the separation capillary is interfaced to an electrokinetic ally pumped nanoelectrospray emitter on a mass spectrometer, and the cathode end and emitter are in contact with an acidic sheath electrolyte;
    (b) filling the anode end of the separation capillary, first, with an alkaline solution, then second, with a mixture comprising an ampholyte and analytes;
    (c) feeding the nanoelectrospray emitter with an acidic solution, wherein the acidic solution feeds into the nanoelectrospray emitter, and wherein the acidic solution comprises a $(C_1-C_8)$ carboxylic acid;
    (d) applying a voltage to the anode and cathode ends of the separation capillary;
    (e) inducing isoelectric focusing of the analytes and chemical mobilization of the analytes toward the cathode end of the separation capillary, wherein the acidic sheath electrolyte is feeding to the emitter during focusing and mobilization; and
    (f) forming a nanoelectrospray, wherein the acidic sheath electrolyte solution ensheaths the mixture flowing out the cathode end of the separation capillary;
    wherein a pH gradient is established by the alkaline solution and the acidic solution to induce isoelectric focusing of the analytes, and as the alkaline solution is titrated to lower pH by the acidic sheath electrolyte solution the analytes are chemically mobilized, then electrokinetically pumped toward the mass spectrometer by the acidic sheath electrolyte solution, thereby forming the nanoelectrospray when the voltage is applied.

2. The method of claim 1 wherein the alkaline solution has a length in the separation capillary of at least 1 cm upon initial filling, and wherein the inner diameter of the capillary is less than 300 μm.

3. The method of claim 2 wherein the alkaline solution comprises ammonium hydroxide.

4. The method of claim 2 wherein the mixture comprising an ampholyte and analytes has a length in the separation capillary of at least 1 cm upon initial filling.

5. The method of claim 1 wherein the acidic solution comprises formic acid.

6. The method of claim 1 wherein the ampholyte has a high buffering capacity per pH unit, a linear pH gradient, and even conductivity across the ampholyte.

7. The method of claim 6 wherein the high buffering capacity per pH unit of the ampholyte ranges from pH 3-10, pH 3-6, pH 5-8, or pH 7-10.

8. The method of claim 1 wherein the acidic sheath electrolyte solution is a chemical mobilizer comprising a $(C_1-C_8)$carboxylic acid that is provided at the cathode end during both capillary isoelectric focusing and chemical mobilization, wherein focusing and mobilization are performed as one-step.

9. The method of claim 1 wherein the acidic sheath electrolyte solution comprises formic acid.

10. The method of claim 9 wherein the acidic sheath electrolyte solution further comprises an alcohol, or acetonitrile.

11. The method of claim 1 wherein the voltage applied for isoelectric focusing and chemical mobilization ranges from about 50 V/cm to about 500 V/cm.

12. The method of claim 1 wherein chemical mobilization automatically follows isoelectric focusing without manual physical manipulation of the separation capillary.

13. The method of claim 1 wherein the separation capillary has an inner surface coated with a polymer.

14. The method of claim 13 wherein the polymer comprises a linear polyacrylamide (LPA).

15. The method of claim 1 wherein the separation capillary has a length of at least 10 cm.

16. The method of claim 1 wherein the outer diameter of the tip of the cathode end of the separation capillary is reduced relative to the outer diameter of the remainder of the separation capillary.

17. The method of claim 16 wherein the outer diameter of the tip of the cathode end of the separation capillary is 20%-50% larger than the inner diameter of the separation capillary.

18. The method of claim 1 wherein the analytes comprise proteins, or drug-protein conjugates.

19. The method of claim 18 wherein the peaks of an electropherogram of proteins, or drug-protein conjugates detected by the mass spectrometer are substantially resolved.

20. The method of claim 19 wherein the electropherogram is substantially reproducible.

\* \* \* \* \*